(12) United States Patent
Gong et al.

(10) Patent No.: US 9,976,000 B2
(45) Date of Patent: May 22, 2018

(54) AQUEOUS GEL

(71) Applicants: NATIONAL UNIVERSITY CORPORATION HOKKAIDO UNIVERSITY, Sapporo-shi, Hokkaido (JP); OSAKA ORGANIC CHEMICAL INDUSTRY LTD., Osaka-shi, Osaka (JP)

(72) Inventors: Jian Ping Gong, Sapporo (JP); Takayuki Kurokawa, Sapporo (JP); Haiyan Yin, Sapporo (JP); Taigo Akasaki, Sapporo (JP); Yoshiyuki Saruwatari, Kashiwara (JP)

(73) Assignees: NATIONAL UNIVERSITY CORP. HOKKAIDO UNIVERSITY, Sapporo-shi (JP); OSAKA ORGANIC CHEMICAL INDUSTRIES LTD., Osaka-shi (JP)

( * ) Notice: Subject to any disclaimer, the term of this patent is extended or adjusted under 35 U.S.C. 154(b) by 187 days.

(21) Appl. No.: 14/535,607

(22) Filed: Nov. 7, 2014

(65) Prior Publication Data
US 2015/0133566 A1    May 14, 2015

Related U.S. Application Data

(63) Continuation of application No. PCT/JP2013/063263, filed on May 13, 2013.

(30) Foreign Application Priority Data

May 12, 2012 (JP) .................. 2012-110133
Nov. 7, 2012 (JP) .................. 2012-245193

(51) Int. Cl.
| | | |
|---|---|---|
| C08J 3/075 | (2006.01) |
| A61K 8/04 | (2006.01) |
| C09D 135/02 | (2006.01) |
| A61K 8/81 | (2006.01) |
| A61Q 19/00 | (2006.01) |

(Continued)

(52) U.S. Cl.
CPC ............... *C08J 3/075* (2013.01); *A61K 8/042* (2013.01); *A61K 8/8158* (2013.01); *A61K 8/8164* (2013.01); *A61K 9/0014* (2013.01); *A61Q 19/00* (2013.01); *C08F 265/10* (2013.01); *C09D 133/26* (2013.01); *C09D 135/02* (2013.01); *C09D 143/02* (2013.01); *C09D 151/003* (2013.01); *A61K 47/32* (2013.01); *C08J 2335/02* (2013.01); *C08L 2201/54* (2013.01); *C12M 25/02* (2013.01); *C12M 25/14* (2013.01)

(58) Field of Classification Search
CPC .. C08F 222/385; C08F 265/10; C08F 220/56; C08F 2220/382; C09D 133/26; C09D 135/02; C09D 151/003; C08L 33/26; C08L 43/02; C08L 2201/54; A61K 47/32; A61K 8/042; A61K 8/8158; A61K 8/8164
See application file for complete search history.

(56) References Cited

U.S. PATENT DOCUMENTS

| | | |
|---|---|---|
| 6,180,118 B1 | 1/2001 | Maubru |
| 2008/0009063 A1 | 1/2008 | Okano et al. |
| 2008/0262181 A1* | 10/2008 | Kitano .................. C08F 220/18 526/312 |

FOREIGN PATENT DOCUMENTS

| | | |
|---|---|---|
| JP | 01-249808 A | 10/1989 |
| JP | 05-140531 A | 6/1993 |

(Continued)

OTHER PUBLICATIONS

International Search Report dated Jul. 30, 2013, issued in corresponding application No. PCT/JP2013/063263.

*Primary Examiner* — Anna Falkowitz
(74) *Attorney, Agent, or Firm* — Westerman, Hattori, Daniels & Adrian, LLP

(57) ABSTRACT

An aqueous gel that is prepared by gelling a polymer components, the polymer components containing polymer A, which is obtained by polymerizing a monomer component containing a betaine monomer represented by the formula (I):

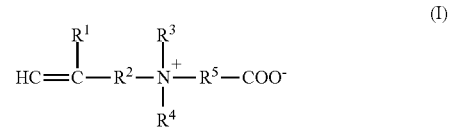

wherein $R^1$ represents hydrogen atom or an alkyl group, $R^2$ represents an alkylene, arylene, aralkylene, —COOH— or —CONH— group; $R^3$ and $R^4$ represent an alkyl group, and $R^5$ represents an alkylene group, and a polymer B, which is obtained by polymerizing a monomer component containing an acidic monomer represented by the formula (II):

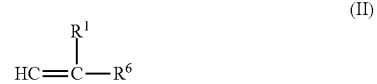

wherein $R^1$ represents hydrogen atom or an alkyl group; $R^6$ represents an optionally neutralized sulfonate group, an optionally neutralized phosphate group, or an alkyl, aryl, aralkyl, carboxyl or amino group carrying an optionally neutralized sulfonate group or an optionally neutralized phosphate group.

19 Claims, 2 Drawing Sheets

(51) Int. Cl.
*C08F 265/10* (2006.01)
*C09D 133/26* (2006.01)
*C09D 143/02* (2006.01)
*A61K 9/00* (2006.01)
*C09D 151/00* (2006.01)
A61K 47/32 (2006.01)
C12M 1/12 (2006.01)

(56) References Cited

FOREIGN PATENT DOCUMENTS

| | | | |
|---|---|---|---|
| JP | 06-200224 | A | 7/1994 |
| JP | 08-109221 | A | 4/1996 |
| JP | 10-101532 | A | 4/1998 |
| JP | 2008-011766 | A | 1/2008 |
| JP | 2009-298971 | A | 12/2009 |
| JP | 2009298971 | * | 12/2009 |
| JP | 2010-057745 | A | 3/2010 |
| WO | 2012/029731 | A1 | 3/2012 |

* cited by examiner

[FIG. 1]
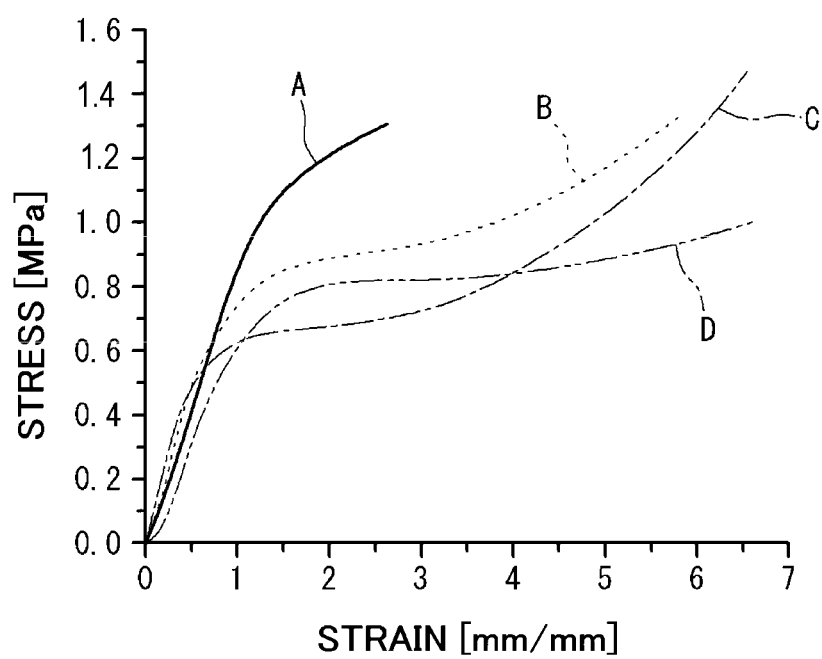

[FIG. 2]
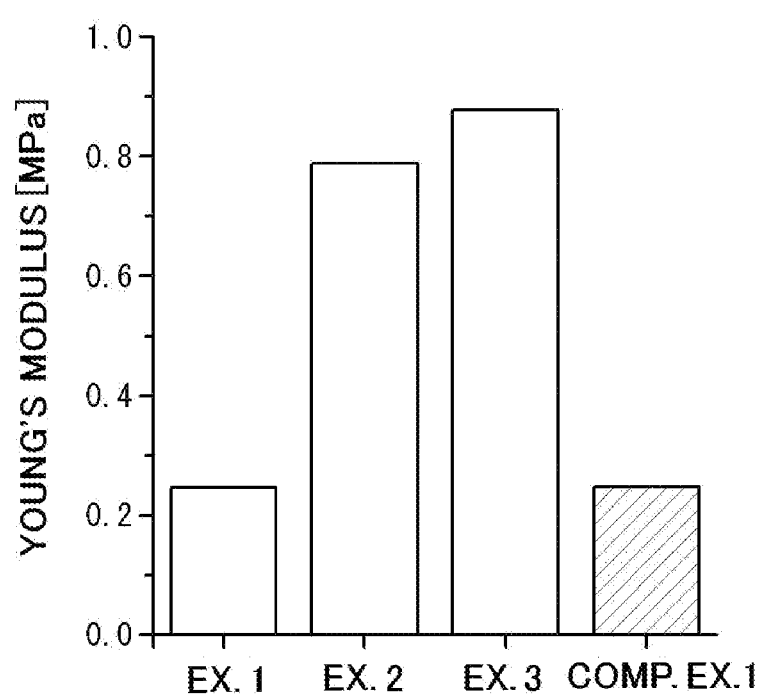

AQUEOUS GEL

TECHNICAL FIELD

The present invention relates to an aqueous gel. More specifically, the present invention relates to an aqueous gel which is expected to be used in, for example, a cell culture sheet, a carrier for immobilizing a medicine, a medical material such as a gel for an adhesive plaster, cosmetics such as a cosmetic pack, a toiletry product such as a paper diaper, a coating material for preventing adhesion of acorn barnacle, a coating material such as various paints, an adhesive gel for a liquid crystal screen protective film, a gel electrolyte for a lithium battery, a transparent actuator material, an electric or electronic material such as a piezoelectric element, and the like.

BACKGROUND ART

As an aqueous gel, for example, sodium polyacrylate obtained by carrying out the polymerization of sodium acrylate and a crosslinkable monomer has been used in, a paper diaper, a gelling agent used in cosmetics, an electrolyte gelling agent used in a lithium battery, and the like. This sodium polyacrylate has an advantage such that the sodium polyacrylate forms a gel having a high viscosity only by the addition in a small amount, due to the repulsion between carboxylic acid ions (—COO-ions) possessed by the polymer and its crosslinking structure. However, when a salt such as sodium chloride which nullifies the repulsion between the above-mentioned carboxylic acid ions (—COO-ions) exists in a gel, repulsion between ions becomes smaller. Therefore, there is a possibility that an aqueous gel made of this sodium polyacrylate itself disintegrates (see, for example, Non-patent Literature 1).

Also, as a cationic thickener, there has been proposed a cationic thickener prepared by carrying out the polymerization of an amine-containing (meth)acrylic monomer, a vinyl monomer, a (meth)acryloyl group-containing monomer and a crosslinkable vinyl monomer (see, for example, Patent Literature 1). When this cationic thickener is used in a small amount, an aqueous gel having a high viscosity can be prepared. However, there is a possibility that this resulting aqueous gel disintegrates when a salt such a sodium chloride exists in the gel, as well as the above-mentioned sodium polyacrylate.

As an aqueous gel which hardly disintegrates even when a salt exists in the gel, there have been known a highly adhesive hydrogel composition prepared by carrying out the polymerization of 2-acrylamido-2-methylpropanesulfonic acid or its salt and a crosslinkable monomer in a polyhydric alcohol and an aqueous medium (see, for example, Patent Literature 2), a gel prepared by using neutralized crosslinkable poly(2-acrylamido-2-methylpropanesulfonic acid) and a gelling agent containing an oxidizing agent (see, for example, Patent Literature 3), and the like. However, the above-mentioned highly adhesive hydrogel composition and the above-mentioned gel do not simultaneously satisfy both of flexibility and mechanical strength.

As a polymer gel which is excellent in mechanical strength, there has been proposed a polymer gel having an interpenetrating network structure made of a physical crosslinking network structure formed by physical crosslinking, a first network structure formed by carrying out the polymerization of a first monomer and crosslinking the resulting polymer, and a second network structure formed by carrying out the polymerization of a second monomer and crosslinking the resulting polymer (see, for example, Patent Literature 4). However, this polymer gel has a defect such that its gel strength is lowered when the polymer gel is charged with positive electric charges.

Also, there have been carried out various attempts for repairing damaged tissues and the like. For example, there have been carried out some attempts such as the use of graft cells such as fetal myocardial cells, skeletal myoblasts or ES cells (embryonic stem cells), in order to repair myocardial tissues damaged by an ischemic cardiac disease such as angina pectoris or cardiac infarction. However, when the graft cells are administered to a tissue in the state of suspension of cells, the injection efficiency of the graft cells is low, and there is a possibility that a recipient tissue is damaged by puncture. Moreover, it has been pointed out that is it difficult that the tissue is repaired in a large area.

Therefore, in recent years, there have been developed a cell structure formed by using a scaffold and a cell sheet produced by molding cells into a sheet. It has been examined that this cell sheet is used as, for example, a cultured epidermal sheet for skin damage due to burn, a corneal epithelial cell sheet for cornea damage, an oral mucous cell sheet used after the excision of esophageal cancer with an endoscope, and the like.

A cell sheet is generally formed on a culture substrate and cells are cultured on the cell sheet. It is necessary that the cell sheet is isolated from the culture substrate when the cell sheet is actually used in treatment. As a process for isolating the cell sheet from the culture substrate, there have been known, for example, a process for isolating the cell sheet from the culture substrate by using a protease such as trypsin, a process for mechanically removing the cell sheet from the culture substrate by using a scraper, a pipette or the like, and the like.

However, according to these methods, when the cell sheet is isolated from the culture substrate, the cell sheet is damaged, or the survival rate of cells is lowered. Therefore, there has been investigated a means which can easily isolate the cell sheet from the culture substrate by improving the material of the culture substrate and its structure. For example, N-isopropylacrylamide (hereinafter, referred to as NIPAM) which is a temperature-responsive polymer has properties such that NIPAM is swollen and becomes liquid at low temperatures, and that its phase transition occurs, and NIPAM is quickly shrunk and gelated at a temperature of around 34° C. Therefore, it has been proposed that cells are cultured on NIPAM which has been gelated at a temperature of 37° C., and the cells which are cultured on the gelated NIPAM are superposed on the other cells which are cultured on the gelated NIPAM, and thereafter, a culture temperature is lowered to 34° C. or lower, to remove NIPAM, and directly superpose the cells (see, for example, Non-patent Literatures 2 to 4). However, since NIPAM is not sufficient in biocompatibility, there is a possibility such that the secretion of an inflammatory protein is accelerated by the adhesion of macrophages to NIPAM during the culturing of cells, and thereby an immunological rejection reaction is caused when NIPAM is applied to a patient.

As a cell culture support, there has been proposed a cell culture support having plural convex portions each of which has a top face and plural concave portions between the plural convex portions, in which the opening of the above-mentioned concave portions has a size to which cells to be cultured cannot be entered, and the above-mentioned cell sheet is removable (see, for example, Patent Literature 5). However, this cell culture support has some defects such that the cell culture support is not suite for producing in a large scale, and that the cell culture support is not inexpensive, as well as the cell culture support is not sufficient in biocompatibility. Therefore, the secretion of an inflammatory protein is accelerated by the adhesion of macrophages to the cell culture support during culturing, and thereby there is a possibility that immunological rejection reaction is generated when the cells are applied to a patient.

As a medical material having a small interaction with biological components such as proteins and hemocytes, and being excellent in biocompatibility, there has been proposed a medical material which is produced by forming a polymer obtained by carrying out the polymerization of a monomer composition containing N-methacryloyloxyethyl-N, N-dimethylammonium-α-N-methylcarboxybetaine on the surface of a substrate (see, for example, Patent Literature 6). It is considered that cells such as macrophages would not be easily adhered to the medical material, because the amount of cells to be adhered is small. However, since the flexibility of its surface is small, there is a possibility that cells will be damaged when the cells which are grown up on the surface of the medical material are removed from the medical material.

PRIOR ART DOCUMENTS

Patent Literatures

Patent Literature 1: Japanese Unexamined Patent Publication No. HEI 05-140531
Patent Literature 2: Japanese Unexamined Patent Publication No. HEI 06-200224
Patent Literature 3: Japanese Unexamined Patent Publication No. HEI 10-101532
Patent Literature 4: Japanese Unexamined Patent Publication No. 2009298971
Patent Literature 5: Japanese Unexamined Patent Publication No. 2008-11766
Patent Literature 6: Japanese Unexamined Patent Publication No. 2010-57745

Non-Patent Literatures

Non-Patent Literature 1: Matao NAKAMURA, "Water-Soluble Polymers", Kagakukogyosha Co., Ltd., 1973
Non-Patent Literature 2: Tatsuya SHIMIZU et al., "Bioscience and Bioindustry", vol 58, page 851, Japanese Bioindustry Association, 2000
Non-Patent Literature 3: Masayuki Yamato et al., "Protein, Nucleic Acid and Enzyme", vol. 45, page 72, KYORITSU SHUPPAN CO., LTD., 2000
Non-Patent Literature 4: Masayuki Yamato et al., "Protein, Nucleic Acid and Enzyme", vol. 64, page 162, KYORITSU SHUPPAN CO., LTD, 2000.

SUMMARY OF THE INVENTION

Problems to be Solved by the Invention

The present invention has been made in view of the above-mentioned prior arts. An object of the present invention is to provide an aqueous gel in which gel strength of the aqueous gel is hardly lowered when a salt exists in the gel, and which is simultaneously satisfied with flexibility and mechanical strength. In addition, an object of present invention is to provide an aqueous gel substrate which is excellent in hydrophilic property and small in adhesiveness to macrophages, and also which is excellent in flexibility. Furthermore, an object of the present invention is to provide a cell culture sheet which is excellent in hydrophilic property and small in adhesiveness to macrophages, which is also excellent in flexibility, and from which grown cells can be easily removed.

Means to Solve the Problems

The present invention relates to:
(1) an aqueous gel prepared by gelling a polymer composition containing a polymer A prepared by carrying out the polymerization of a monomer composition containing a betaine monomer represented by the formula (I):

[Chemical formula 1]

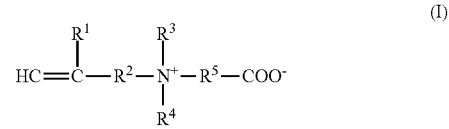

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition containing an acidic monomer represented by the formula (II):

[Chemical formula 2]

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof: an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

(2) the aqueous gel according to the above-mentioned item (1), wherein in the betaine monomer represented by the formula (I), $R^1$ is hydrogen atom or an alkyl group having 1 to 6 carbon atoms which may have hydroxyl group or a halogen atom: $R^2$ is —COO— group or —CONH— group; each of $R^3$ and $R^4$ is methyl group, respectively; and $R^5$ is methylene group;

(3) the aqueous gel according to the above-mentioned item (1) or (2), wherein the molar ratio of the functional group of the polymer A to the functional group of the polymer B is 0.5/1 to 1.5/1;

(4) a medical material in which the aqueous gel according to any one of the above-mentioned items (1) to (3) is used;

(5) a cosmetic composition in which the aqueous gel according to any one of the above-mentioned items (1) to (3) is used;

(6) a toiletry article in which the aqueous gel according to any one of the above-mentioned items (1) to (3) is used;

(7) a coating material in which the aqueous gel according to any one of the above-mentioned items (1) to (3) is used;

(8) an electric or electronic material in which the aqueous gel according to any one of the above-mentioned items (1) to (3) is used; and (9) a process for producing an aqueous gel, which includes carrying out a solution-polymerization of an aqueous solution of a monomer composition containing an acidic monomer to give polymer B, mixing the resulting polymer B with an aqueous solution of a monomer composition containing a betaine monomer so as to form a homogeneous mixture, and carrying out a solution-polymerization of the resulting mixture to prepare a polymer A; or carrying out a solution-polymerization of an aqueous solution of a monomer composition containing a betaine monomer to give a polymer A, mixing the resulting polymer A with a monomer composition containing an acidic monomer so as to form a homogeneous mixture, and carrying out the solution-polymerization of the resulting mixture to prepare a polymer B.

In addition, the present invention relates to:

(1) an aqueous gel substrate containing a crosslinked polymer prepared by carrying out the polymerization of a monomer composition containing a hydrophilic monomer represented by the formula (III):

[Chemical formula 3]

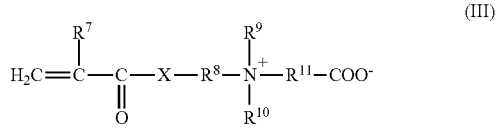

(III)

wherein $R^7$ is hydrogen atom or an alkyl group having 1 to 4 carbon atoms $R^8$ is an alkylene group having 1 to 8 carbon atoms; each of $R^9$ and $R^{10}$ is independently an alkyl group having 1 to 4 carbon atoms, $R^{11}$ is an alkylene group having 1 to 4 carbon atoms, and X is oxygen atom or —NH— group,
and a crosslinkable monomer; as an effective component;

(2) the aqueous gel substrate according to the above-mentioned item (1), wherein the crosslinkable monomer is at least one monomer selected from the group consisting of a (meth)acrylamide compound having two or more (meth) acryloyl groups, a (meth)acrylate compound having two or more (meth)acryloyl groups, a (meth)acrylate compound having two or more carbon-carbon double bonds and an aromatic compound having two or more carbon-carbon double bonds;

(3) the aqueous gel substrate according to the above-mentioned item (1) or (2), wherein in the formula (III), $R^7$ is methyl group; $R^8$ is ethylene group; each of $R^9$ and $R^{10}$ is methyl group; $R^{11}$ is methylene group; and X is oxygen atom; and (4) a cell culture sheet, in which the aqueous gel substrate according to any one of the above-mentioned items (1) to (3) is used as a substrate.

Effects of the Invention

The aqueous gel of the present invention exhibits excellent effects such that gel strength of the aqueous gel is hardly lowered even when a salt exists in the gel, and that flexibility and mechanical strength are simultaneously satisfied. In addition, the aqueous gel substrate of the present invention exhibits excellent effects such that the aqueous gel substrate is excellent in hydrophilic property and small in adhesiveness to macrophages, and that the aqueous gel substrate is also excellent in flexibility. Furthermore, the cell culture sheet of the present invention exhibits excellent effects such that the cell culture sheet is excellent in hydrophilic property, and small in adhesiveness to macrophages, and that the cell culture sheet is also excellent in flexibility since the above-mentioned aqueous gel substrate is used in the cell culture sheet. Therefore, grown cells can be easily removed from the cell culture sheet.

BRIEF EXPLANATION OF DRAWINGS

FIG. 1 is a graph showing the results of measurement of the tensile strength of samples 1 to 3 obtained in Examples 1 to 3 and a comparative sample 1 obtained in Comparative Example 1.

FIG. 2 is a graph showing the results of measurement of the Young's modulus of samples 1 to 3 obtained in Examples 1 to 3 and a comparative sample obtained in Comparative Example 1.

EMBODIMENTS FOR CARRYING OUT THE INVENTION

As described above, the aqueous gel of the present invention is prepared by gelling a polymer composition containing a polymer A prepared by carrying out the polymerization of a monomer composition containing a betaine monomer represented by the formula (I):

[Chemical formula 4]

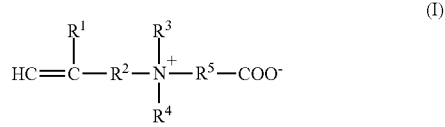

(I)

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms,
and a polymer B prepared by carrying out the polymerization of a monomer composition containing an acidic monomer represented by the formula (II):

[Chemical formula 5]

(II)

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof, carboxyl group having sulfonic acid group or a neutralized group thereof, or phosphoric acid group or a neutralized group thereof, or phosphoric acid group or a neutralized group thereof.

Since the aqueous gel of the present invention is formed from the above-mentioned polymer A and the above-mentioned polymer B, the gel strength of the aqueous gel is hardly lowered even when a salt exists in the gel, and the aqueous gel is simultaneously satisfied with flexibility and mechanical strength. The reason why the aqueous gel of the present invention shows the above excellent properties are supposed to be based upon that the aqueous gel has a network structure formed by penetrating the polymer A and the polymer B into each other due to the interaction between the polymer A and the polymer B. More specifically, it is considered that an aqueous gel which is strong and excellent in flexibility can be obtained, since the amino group of the polymer A and the acidic group of polymer B are interacted with each other due to the combined use of the network structure of the polymer A derived from a betaine monomer which is electrically neutral and the network structure of the polymer B derived from the acidic monomer which shows acidity.

The polymer A is obtained by carrying out the polymerization of a monomer composition containing the betaine monomer represented by the formula (I).

In the formula (I), $R^1$ is hydrogen atom or an alkyl group having 1 to 6 carbon atoms which may have hydroxyl group or a halogen atom. $R^1$ is more specifically hydrogen atom, an alkyl group having 1 to 6 carbon atoms, an alkyl group of 1 to 6 carbon atoms having hydroxyl group or an alkyl group of 1 to 6 carbon atoms having a halogen atom. The alkyl group having 1 to 6 carbon atoms includes, for example, methyl group, ethyl group, n-propyl group, isopropyl group, n-butyl group, isobutyl group, tert-butyl group and the like, and the present invention is not limited only to those exemplified ones. The alkyl group of 1 to 6 carbon atoms having hydroxyl group includes, for example, hydroxymethyl group, hydroxyethyl group, hydroxy-n-propyl group, hydroxyisopropyl group, hydroxy-n-butyl group, hydroxyisobutyl group, hydroxy-tert-butyl group and the like, and the present invention is not limited only to those exemplified ones. The alkyl group of 1 to 6 carbon atoms having a halogen atom includes, for example, trifluoromethyl group, trifluoroethyl group, trifluoro-n-propyl group, trifluoroisopropyl group, trifluoro-n-butyl group, trifluoroisobutyl group, trifluoro-tert-butyl group, trichloromethyl group, trichloroethyl group, trichloro-n-propyl group, trichloroisopropyl group, trichloro-n-butyl group, trichloroisobutyl group, trichloro-tert-butyl group and the like, and the present invention is not limited only to those exemplified ones. Among the groups of $R^1$, hydrogen atom or an alkyl group having 1 to 6 carbon atoms which may have a hydroxyl group or a halogen atom is preferred.

In the formula (I), $R^2$ is an alkylene group having 1 to 6 carbon atoms which may have hydroxyl group, an arylene group having 6 to 12 carbon atoms, an aralkylene group having 7 to 12 carbon atoms, —COO— group or —CONH— group. $R^2$ is more specifically an alkylene group having 1 to 6 carbon atoms, an alkylene group of 1 to 6 carbon atoms having hydroxyl group, an arylene group having 6 to 12 carbon atoms, an aralkylene group having 7 to 12 carbon atoms, —COO— group or —CONH— group. The alkylene group having 1 to 6 carbon atoms includes, for example, methylene group, ethylene group, n-propylene group, isopropylene group, n-butylene group, isobutylene group, tert-butylene group and the like, and the present invention is not limited only to those exemplified ones. The alkylene group of 1 to 6 carbon atoms having hydroxyl group includes, for example, hydroxymethylene group, hydroxyethylene group, hydroxy-n-propylene group, hydroxyisopropylene group, hydroxy-n-butylene group, hydroxyisobutylene group, hydroxy-tert-butylene group and the like, and the present invention is not limited only to those exemplified ones. The arylene group having 6 to 12 carbon atoms includes, for example, phenylene group, an alkylphenyl group having an alkyl group of 1 to 4 carbon atoms, naphthylene group and the like, and the present invention is not limited only to those exemplified ones. Among the groups of $R^2$, —COO— group and —CONH— group are preferred, and —CONH— group is more preferred.

In the formula (I), each of $R^3$ and $R^4$ is independently an alkyl group having 1 to 18 carbon atoms. The alkyl group having 1 to 18 carbon atoms includes, for example, methyl group, ethyl group, n-propyl group, isopropyl group, n-butyl group, isobutyl group, tert-butyl group and the like, and the present invention is not limited only to those exemplified ones. Among the groups of $R^2$, an alkyl group having 1 to 4 carbon atoms is preferred, and methyl group is more preferred, from the viewpoint of improvement in industrial productivity of the betaine monomer represented by the formula (I).

In the formula (I), $R^5$ is an alkylene group having 1 to 8 carbon atoms. The alkylene group having 1 to 8 carbon atoms includes, for example, methylene group, ethylene group, n-propylene group, isopropylene group, n-butylene group, isobutylene group, tert-butylene group and the like, and the present invention is not limited only to those exemplified ones. Among the groups of $R^5$, an alkylene group having 1 to 6 carbon atoms is preferred, an alkylene group having 1 to 4 carbon atoms is more preferred, and methylene group is still more preferred, from the viewpoint of facility in formation of a neutralized salt from an obtained betaine polymer.

In the betaine monomer represented by the formula (I), it is preferred that $R^1$ is hydrogen atom or an alkyl group having 1 to 6 carbon atoms which may have hydroxyl groups or a halogen atom. $R^2$ is —COO— group or —CONH— group, each of $R^3$ and $R^4$ is methyl group, and $R^5$ is methylene group.

The betaine monomer represented by the formula (I) includes, for example, N-acryloyloxyethyl-N,N-dimethylammonium-α-N-methylcarboxybetaine, N-methacryloyloxyethyl-N,N-dimethylammonium-α-N-methylcarboxybetaine, N-acryloyloxyethyl-N,N-diethylammonium-α-N-methylcarboxybetaine, N-methacryloyloxyethyl-N,N-diethylammonium-α-N-methylcarboxybetaine, N-acryloyloxyethyl-N,N-dimethylammonium-β-N-ethylcarboxybetaine, N-methacryloyloxyethyl-N,N-dimethylammonium-β-N-ethylcarboxybetaine, N-acryloyloxyethyl-N,N-diethylammonium-β-N-ethylcarboxybetaine, N-methacryloyloxyethyl-N,N-diethylammonium-β-N-ethylcarboxybetaine, N-acrylamidopropyl-N,N-dimethylammonium-α-N-methylcarboxybetaine, N-acrylamidopropyl-N,N-diethylammonium-α-N-methylcarboxybetaine, N-acrylamidopropyl-N,N-diethylammonium-α-N-methylcarboxybetaine, N-methacrylamidopropyl-N,N-dimethylammonium-α-N-methylcarboxybetaine, N-acrylamidopropyl-N,N-dimethylammonium-β-N-ethylcarboxybetaine, N-methacrylamidopropyl-N,N-dimethylammonium-β-N-ethylcarboxybetaine, N-acrylamidopropyl-N,N-diethylammonium-β-N-ethylcarboxybetaine, N-methacrylamidopropyl-N,N-diethylammonium-β-N-ethylcarboxybetaine and the like, and the present invention is not limited only to those exemplified ones. These betaine monomers can be used alone, respectively, or two or more kinds thereof can be used together. The betaine monomers can be easily prepared by the methods as described in, for example, Japanese Unexamined Patent Publication No. HEI 09-95474, Japanese Unexamined Patent Publication No. HEI 09-95586, Japanese Unexamined Patent Publication No. HEI 11-222470, and the like.

The polymer A is obtained by carrying out the polymerization of a monomer composition containing the betaine monomer. The monomer composition can be composed of only the betaine monomer, or may contain a neutral monomer other than the betaine monomer.

Incidentally, in the present specification, the neutral monomer does not mean that the monomer itself is neutral, but means a monomer which does not impart an acidic group and a basic group to the polymer a, when the polymer A is formed by copolymerization of the neutral monomer and the betaine monomer.

The neutral monomer includes, for example, monofunctional monomers such as alkyl (meth)acrylate having a alkyl group of 1 to 18 carbon atoms, such as methyl acrylate, methyl methacrylate, ethyl acrylate, ethyl methacrylate, n-butyl acrylate, n-butyl methacrylate, isobutyl acrylate, isobutyl methacrylate, tert-butyl acrylate, tert-butyl methacrylate, neopentyl acrylate, neopentyl methacrylate, octyl acrylate, octyl methacrylate, lauryl acrylate, lauryl methacrylate, stearyl acrylate, stearyl methacrylate, cetyl acrylate and cetyl methacrylate; cycloalkyl (meth)acrylates having a cycloalkyl group of 6 to 12 carbon atoms, such as cyclohexyl acrylate and cyclohexyl methacrylate; aryl (meth)acrylate having an aryl group of 6 to 12 carbon atoms, such as benzyl acrylate and benzyl methacrylate; hydroxyalkyl (meth)acrylates having a hydroxyalkyl group of 2 to 6 carbon atoms, such as hydroxyethyl acrylate, hydroxyethyl methacrylate, hydroxypropyl acrylate, hydroxypropyl methacrylate, hydroxybutyl acrylate and hydroxybutyl methacrylate; alkoxyalkyl (meth)acrylates having an alkoxyalkyl group of 2 to 8 carbon atoms, such as methoxyethyl acrylate, methoxyethyl methacrylate, methoxybutyl acrylate, and methoxybutyl methacrylate; alkylcarbitol (meth)acrylates having an alkyl group of 1 to 4 carbon atoms, such as ethylcarbitol acrylate and ethylcarbitol methacrylate; alkyl (meth)acrylamides having an alkyl group of 1 to 12 carbon atoms, such as N-methylacrylamide, N-methylmethacrylamide, N-ethylacrylamide, N-ethylmethacrylamide, N-propylacrylamide, N-propylmethacrylamide, N-isopropylacrylamide, N-isopropylmethacrylamide, N-tert-butylacrylamide, N-tert-butylmethacrylamide, N-octylacrylamide, N-octylmethacrylamide, N,N-dimethylacrylamide, N,N-dimethylmethacrylamide, N,N-diethylacrylamide and N,N-diethylmethacrylamide; alkoxy(meth)acrylamides having an alkoxy group of 1 to 6 carbon atoms, such as N-butoxymethylacrylamide and N-butoxymethylmethacrylamide; (meth)acryloylmorpholines such as acryloylmorpholine and methacryloylmorpholine; diacetone (meth)acrylamides such as diacetoneacrylamide and diacetonemethacrylamide; styrenic monomers such as styrene and methylstyrene; fatty acid alkyl esters having an alkyl group of 1 to 4 carbon atoms other than the alkyl (meth)acrylates, such as methyl itaconate and ethyl itaconate; fatty acid vinyl esters such as vinyl acetate and vinyl propionate; nitrogen atom-containing monomers such as N-vinylpyrrolidone and N-vinylcaprolactam;

polyfunctional monomers such as di- or tri(meth)acrylates such as ethylene diacrylate, ethylene dimethacrylate, ethylene glycol diacrylate, ethylene glycol dimethacrylate, ethylene glycol diacrylate, ethylene glycol dimethacrylate, 1,4-butanediol diacrylate, 1,4-butanediol dimethacrylate, 1,6-hexanediol diacrylate, 1,6-hexanediol dimethacrylate, 1,9-nonanediol diacrylate, 1,9-nonanediol dimethacrylate, 2-n-butyl-2-ethyl-1,3-propanediol di(meth)acrylate, tripropylene glycol di(meth)acrylate, tetraethylene glycol di(meth)acrylate, trimethylolpropane tri(meth)acrylate and pentaerythritol tri(meth)acrylate; (meth)acrylamides having two or more carbon-carbon double bonds, such as bismethyleneacrylamide and bismethylenemethacrylamide; aromatic compounds having two or more carbon-carbon double bonds, such as divinylbenzene and diallylbenzene; amine compounds having two or more allyl groups, such as triallylamine; (meth)acrylamide compounds having two or more carbon-carbon double bonds, such as methylenebisacrylamide and methylenebismethacrylamide, and the present invention is not limited only to those exemplified ones. These neutral monomers can be used alone, respectively, or two or more kinds thereof can be used together.

In the present specification, "(meth)acry" means "acry" or "methacry".

The content of the neutral monomer in the monomer composition containing the betaine monomer is not particularly limited. The content of the neutral monomer in the monomer composition containing the betaine monomer is preferably 20% by weight or more, and more preferably 50% by weight or more, from the viewpoint of imparting a property based on the neutral monomer to a polymer, and is preferably 90% by weight or less, and more preferably 70% by weight or less, from the viewpoint of improvement in interaction based on the betaine monomer. In addition, the content of the betaine monomer in the monomer composition containing the betaine monomer is not particularly limited. The betaine monomer in the monomer composition containing the betaine monomer is preferably 10% by weight or more, and more preferably 30% by weight or more, from the viewpoint of improvement in interaction based on the betaine monomer, and is preferably 80% by weight or less, and more preferably 50% by weight or less, from the viewpoint of imparting a property based on the neutral monomer to a polymer.

The atmosphere where the monomer composition containing the betaine monomer is polymerized is not particularly limited, and can be the air, or an inert gas such as nitrogen gas or argon gas.

The polymerization of the monomer composition containing the betaine monomer can be carried out, for example, by a mass polymerization method, a solution polymerization method or the like. When the moment composition containing the betaine monomer is polymerized by a solution polymerization method, a solvent is used. The solvent includes, for example, water; alcohols such as methyl alcohol, ethyl alcohol, isopropyl alcohol, ethylene glycol and propylene glycol; ketones such as acetone and methyl ethyl ketone; alkyl ethers such as diethyl ether and tetrahydrofuran; aromatic compounds such as benzene, toluene and xylene; hydrocarbon compounds such as n-hexane and cyclohexane; acetates such as methyl acetate and ethyl acetate, and the present invention is not limited only to those exemplified ones. These solvents can be used alone, respectively, or two or more kinds thereof can be used together. The amount of the solvent cannot be absolutely determined since the amount differs depending on the kind of the solvent. The amount of the solvent is usually preferably 300 to 1000 parts by weight or so per 100 parts by weight of the monomer composition containing the betaine monomer.

The polymerization of the monomer composition containing the betaine monomer can be carried out, for example, by a polymerization method such as a radical polymerization method, a living radical polymerization method, an anion polymerization method, a cation polymerization method, an addition polymerization method or a condensation polymerization method.

When the monomer composition containing the betaine monomer is polymerized, a polymerization initiator can be used. The polymerization initiator includes, for example, a thermal polymerization initiator and a photopolymerization initiator.

The thermal polymerization initiator includes, for example, azo-based polymerization initiators such as azoisobutyronitrile, methyl azoisobutyrate and azobisdimethylvaleronitrile; and peroxide-based polymerization initiators such as benzoyl peroxide, potassium persulfate and ammonium persulfate, and the present invention is not limited only to those exemplified ones. These thermal polymerization initiators can be used alone, respectively, or two or more kinds thereof can be used together.

When the thermal polymerization initiator is used as a polymerization initiator, it is preferred that the amount of the thermal polymerization initiator is usually 0.01 to 20 parts by weight or so per 100 parts by weight of the monomer composition containing the betaine monomer.

The photopolymerization initiator includes, for example, 2-oxoglutaric acid, 1-hydroxycyclohexyl phenyl ketone, 2-hydroxy-2-methyl-1-phenylpropan-1-one, 2-methyl-[4-(methylthio)phenyl]-2-morpholinopropan-1-one, 2,2-dimethoxy-1,2-diphenylethan-1-one, benzophenone, 1-[4-(2-hydroxyethoxy)phenyl]-2-hydroxy-2-methyl-1-propan-1-one, 2-benzyl-2-dimethylamino-1-(4-morpholinophenyl)butan-1-one, bis(2,6-dimethoxybenzoyl)-2,4,4-trimethylpentylphosphine oxide and the like, and the present invention is not limited only to those exemplified ones. These photopolymerization initiators can be used alone, respectively, or two or more kinds thereof can be used together.

When the photopolymerization initiator is used as a polymerization initiator, it is preferred that the amount of the photopolymerization initiator is usually 0.01 to 20 parts by weight or so per 100 parts by weight of the monomer composition containing the betaine monomer.

The polymerization temperature of the monomer composition containing the betaine monomer is not particularly limited, and can be usually a temperature of 5 to 80° C. or so. The period of time necessary for the polymerization of the monomer composition containing the betaine monomer cannot be absolutely determined, because the period of time for the polymerization differs depending on the polymerization conditions. Therefore, the period of time for the polymerization is arbitrary. The polymerization reaction can be arbitrarily terminated at the time when the amount of the remaining monomer attains to 10% by weight or less. The amount of the remaining monomer can be determined, for example, by adding bromine to the double bond of the monomer, and measuring the content of the double bond.

As described above, the polymer A is obtained by carrying out the polymerization of the monomer composition containing the betaine monomer.

The polymer B is obtained by carrying out the polymerization of the monomer composition containing the acidic monomer represented by the formula (II).

In the present specification, the acidic monomer means a monomer having a high ionization degree in an aqueous solution of the acidic monomer. More specifically, the acidic monomer means a monomer having an acid dissociation constant (pKa) of 0 or less in an aqueous solution of the acidic monomer.

In the present invention, since the acid monomer is used in the monomer composition as a raw material of the polymer B, and the polymer B has a strong force to release a proton, there is exhibited an excellent property such that the monomer composition is hardly affected by a salt in comparison with the case where a carboxylic acid is used in the monomer composition. The reason why the above excellent property is exhibited is as follows: When a salt made of a strong acid and a strong base, such as sodium chloride is contained in the monomer composition, since the —COO— group of a carboxylic acid contained in a monomer composition is formed into —COO— group, and the repulsion of ions is reduced, a resulting polymer comes to be shrunk. In contrast, in the case of the acidic monomer, since the acidic monomer has an ionization degree higher than a carboxylic acid, and the difference between the ionization degree of the acidic monomer and that of sodium chloride is smaller, it is thought that the shrinking of a resulting polymer becomes smaller.

In the formula (II), $R^1$ is hydrogen atom or an alkyl group having 1 to 6 carbon atoms which may have hydroxyl group or a halogen atom. The group $R^1$ is specifically hydrogen atom, an alkyl group having 1 to 6 carbon atoms, an alkyl group of 1 to 6 carbon atoms having hydroxyl group or an alkyl group of 1 to 6 carbon atoms having a halogen atom. The alkyl group having 1 to 6 carbon atoms includes, for example, methyl group, ethyl group, n-propyl group, isopropyl group, n-butyl group, isobutyl group, tert-butyl group and the like, and the present invention is not limited only to those exemplified ones. The alkyl group of 1 to 6 carbon atoms having hydroxyl group includes, for example, hydroxymethyl group, hydroxyethyl group, hydroxy-n-propyl group, hydroxyisopropyl group, hydroxy-n-butyl group, hydroxyisobutyl group, hydroxy-tert-butyl group and the like, and the present invention is not limited only to those exemplifies ones. The alkyl group of 1 to 6 carbon atoms having a halogen atom includes, for example, trifluoromethyl group, trifluoroethyl group, trifluoro-n-propyl group, trifluoroisopropyl group, trifluoro-n-butyl group, trifluoroisobutyl group, trifluoro-tert-butyl group, trichloromethyl group, trichloroethyl group, trichloro-n-propyl group, trichloroisopropyl group, trichloro-n-butyl group, trichloroisobutyl group, trichloro-tert-butyl group and the like, and the present invention is not limited only to those exemplified ones.

In the formula (II), $R^6$ is sulfonic acid group or a neutralized group thereof; phosphoric acid group or a neutralized group thereof; an alkyl group of 1 to 6 carbon atoms having sulfonic acid group or a neutralized group thereof, or phosphoric acid group or a neutralized group thereof, which may have a halogen atom; an aryl group of 6 to 12 carbon atoms having sulfonic acid group or a neutralized group thereof, or phosphoric acid group or a neutralized group thereof; an aralkyl group of 7 to 12 carbon atoms having sulfonic acid group or a neutralized group thereof, or phosphoric acid group or a neutralized group thereof, carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

The acidic monomer represented by the formula (II) includes, for example, a vinyl monomer having sulfone group, a vinyl monomer having nitric acid group ($-NO_3$ group) and the like. Incidentally, a vinyl monomer having phosphoric acid group, which is an oxo acid, has an acid dissociation constant (pKa) of 0 or more, and is included in the acidic monomer according to the Pauling's rules.

Concrete examples of the acidic monomer represented by the formula (II) include vinylsulfonic acid, styrene parasulfonic acid, allylsulfonic acid, acrylamidomethylpropanesulfonic acid, methacrylamidomethylpropanesulfonic acid, ethylene oxide-modified phosphoric acid acrylate and ethylene oxide-modified phosphoric acid acrylate, and the present invention is not limited only to those exemplifies ones. These acidic monomers can be used alone, respectively, or two or more kinds thereof can be used together. Among these acidic monomers, vinylsulfonic acid, styrene parasulfonate, acrylamidomethylpropanesulfonic acid and methacrylamidomethylpropanesulfonic acid are preferred from the viewpoint of improvement in stability as a monomer, and improvement in industrial productivity.

The polymer B is obtained by carrying out the polymerization of the monomer composition containing the acidic monomer. The monomer composition can be composed of only the acidic monomer, or may contain a neutral monomer other than the acidic monomer.

As the neutral monomer, there can be exemplified the same neutral monomers as those used in the above-mentioned monomer composition containing a betaine monomer. The neutral monomers can be used alone, or two or more kinds thereof can be used together.

The content of the neutral monomer in the monomer composition containing the acidic monomer is not particularly limited. The content of the neutral monomer is preferably 20% by weight or more, more preferably 50% by weight or more, from the viewpoint of imparting a property based on the neutral monomer to a polymer, and preferably 95% by weight or less, more preferably 90% by weight or less, from the viewpoint of improvement in a property based on the acidic monomer. In addition, the content of the acidic monomer in the monomer composition containing the acidic monomer is not particularly limited. The content of the acidic monomer is preferably 5% by weight or more, more preferably 10% by weight or more, from the viewpoint of improvement in a property based on the acidic monomer, and preferably 80% by weight or less, more preferably 50% by weight or less, from the viewpoint of imparting a property based on the neutral monomer to a polymer.

When the monomer composition containing the acidic monomer is polymerized, the atmosphere is not particularly limited. The atmosphere can be the atmospheric air or an inert gas such as nitrogen gas or argon gas.

The polymerization of the monomer composition containing the acidic monomer can be carried out by, for example, a mass polymerization method, a solution polymerization method and the like. When the monomer composition containing the acidic monomer is polymerized by a solution polymerization method, a solvent is used. The solvent includes, for example, water; alcohols such as methyl alcohol, ethyl alcohol, isopropyl alcohol, ethylene glycol and propylene glycol; ketones such as acetone and methyl ethyl ketone; alkyl ethers such as diethyl ether and tetrahydrofuran; aromatic compounds such as benzene, toluene and xylene; hydrocarbon compounds such as n-hexane and cyclohexane; acetic acid esters such as methyl acetate and ethyl acetate, and the present invention is not limited only to those exemplified ones. These solvents can be used alone, respectively, or two or more kinds thereof can be used together. The amount of the solvent cannot be absolutely determined because the amount of the solvent is different depending on the kind of the solvent. It is preferred that the amount of the solvent is usually 300 to 1000 parts by weight or so per 100 parts by weight of the monomer composition containing the acidic monomer.

The polymerization of the monomer composition containing the acidic monomer can be carried out by, for example, a polymerization method such as a radical polymerization method, a living radical polymerization method, an anion polymerization method, a cation polymerization method, an addition polymerization method or a condensation polymerization method.

When the monomer composition containing the acidic monomer is polymerized, a polymerization initiator can be used. The polymerization initiator includes, for example, a thermal polymerization initiator, a photopolymerization initiator and the like. As the thermal polymerization initiator and the photopolymerization initiator, the same thermal polymerization initiator and photopolymerization initiator as those used in the above-mentioned monomer composition containing the betaine monomer can be exemplified.

In any case where the thermal polymerization initiator or the photopolymerization initiator is used, it is preferred that the amount of the polymerization initiator is usually 0.01 to 20 parts by weight or so per 100 parts by weight of the monomer composition containing the acidic monomer.

The polymerization temperature of the monomer composition containing the acidic monomer is not particularly limited, and can be usually a temperature of 5 to 80° C. or so. The period of time necessary for the polymerization of the monomer composition containing the acidic monomer cannot be absolutely determined because the period of time for the polymerization differs depending on the polymerization conditions. Therefore, the period of time for the polymerization is arbitrary. The polymerization reaction can be arbitrarily terminated at the time when the amount of the remaining monomer becomes 10% by weight or less. The amount of the remaining monomer can be determined, for example, by adding bromine to the double bond of the monomer, and determining the content of a double bond.

As described above, the polymer B is obtained by carrying out the polymerization of the monomer composition containing the acidic monomer.

The aqueous gel of the present invention is obtained by gelling a polymer composition containing the polymer A obtained by carrying out the polymerization of the monomer composition containing a betaine monomer and the polymer B obtained by carrying out the polymerization of the monomer composition containing an acidic monomer.

The molar ratio of the functional group of the polymer A to the functional group of the polymer B is preferably 0.5/1 or more from the viewpoint of improvement in gel strength, and preferably 1.5/1 or less from the viewpoint of enhancement in elasticity of a gel. The functional group of the polymer A and the functional group of the polymer B specifically mean COO— group of the polymer A and $R^6$ group of the polymer B.

As a suitable process for producing the aqueous gel of the present invention, there can be cited, for example, a process for producing an aqueous gel, which includes carrying out a solution-polymerization of an aqueous solution of the monomer composition containing the acidic monomer, thereafter mixing the resulting polymer B with an aqueous solution of the monomer composition containing the betaine monomer so as to be uniform, and carrying out the solution polymerization of the resulting mixture to give the polymer A; a process for producing an aqueous gel, which includes carrying out a solution-polymerization of an aqueous solution of the monomer composition containing the betaine monomer, thereafter mixing the resulting polymer A with the monomer composition containing the acidic monomer so as to be uniform, and carrying out the solution polymerization of the resulting mixture to give the polymer B; and the like. The present invention is not limited only to those exemplified methods. Among these methods, the former method is preferred from the viewpoint of improvement in industrial productivity.

The aqueous gel of the present invention obtained in the above exhibits excellent effects such that gel strength of the aqueous gel is hardly lowered even when a salt exists in the gel, and that flexibility and mechanical strength are simultaneously satisfied. Therefore, it is expected that the aqueous gel of the present invention is used in, for example, a cell culture sheet, a carrier for immobilizing a medicine, a medical material such as a gel for an adhesive plaster, cosmetics such as a cosmetic pack, a toiletry product such as a paper diaper, a coating material for preventing the adhesion of acorn barnacle, coating materials such as various paints, an adhesive gel for a liquid crystal protective film, a gel electrolyte for a lithium battery, a transparent actuator material, an electric or electronic material such as a piezoelectric element, and the like.

In addition, as described above, the aqueous gel substrate of the present invention is characterized in that the aqueous gel substrate contains as an effective component, a crosslinked polymer obtained by carrying out the polymerization of a monomer composition containing a hydrophilic monomer represented by the formula (III):

[Chemical formula 6]

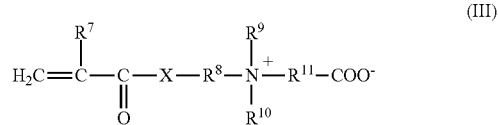

(III)

wherein $R^7$ is hydrogen atom or an alkyl group having 1 to 4 carbon atoms, $R^8$ is an alkylene group having 1 to 8 carbon atoms, each of $R^9$ and $R^{10}$ is independently an alkyl group having 1 to 4 carbon atoms, $R^{11}$ is an alkylene group having 1 to 4 carbon atoms, and X is oxygen atom or —NH— group, and a crosslinkable monomer.

In the present specification, the phrase "contains a crosslinked polymer as an effective component" means that the aqueous gel substrate of the present invention contains a crosslinked polymer as an effective component, and moreover may contain a component other than the crosslinked polymer within a scope which would not hinder an object of the present invention.

Since the above-mentioned crosslinked polymer is used in the aqueous gel substrate of the present invention, the aqueous gel substrate is not only excellent in hydrophilic property, but also small in adhesiveness to macrophages and excellent in flexibility. In addition, since the aqueous gel substrate is used in the cell culture sheet of the present invention, the cell culture sheet is not only excellent in hydrophilic property, but also small in adhesiveness to macrophages and further excellent in flexibility. Therefore, grown cells can be easily removed from the cell culture sheet.

The reason why the aqueous gel substrate and cell culture sheet of the present invention exhibit the above excellent properties is not clear, but is conceived to be probably based on the following reasons:

According to a conventional cell culture sheet, it is conceived that macrophages are directly contacted with a cell culture sheet, and therefore, the microphages adhere to the cell culture sheet. In contrast, according to the aqueous gel substrate and cell culture sheet of the present invention, the crosslinked polymer used in the aqueous gel substrate is excellent in hydrophilic property. Moreover, microphage is prevented from the direct contact with an aqueous gel substrate when the macrophages are placed on the surface of the aqueous gel substrate, because a thin water film exists on the surface of the aqueous gel substrate. Therefore, it is conceived that macrophages are prevented from the direct adhesion to the cell culture sheet. Furthermore, since the cell culture sheet of the present invention is also excellent in flexibility, cells can be easily removed from the cell culture sheet by using, for example, tweezers.

Accordingly, the aqueous gel substrate of the present invention is excellent in hydrophilic property, and has a high compatibility with water. Therefore, a water film is easily formed on the surface of the aqueous gel substrate, and moreover the aqueous gel substrate itself has a property such that the aqueous gel substrate forms a thin water film on its surface. Accordingly, since the adhesion of microphages to the aqueous gel substrate can be avoided by the water film formed on its surface, the aqueous gel substrate of the present invention can be suitably used as a cell culture sheet.

The aqueous gel substrate of the present invention contains a crosslinked polymer as an effective component. The crosslinked polymer is obtained by carrying out the polymerization of a monomer composition containing a hydrophilic monomer represented by the formula (III) and a crosslinkable monomer.

In the hydrophilic monomer represented by the formula (III), $R^7$ is hydrogen atom or an alkyl group having 1 to 4 carbon atoms. The alkyl group having 1 to 4 carbon atoms includes, for example, methyl group, ethyl group, n-propyl group, isopropyl group, n-butyl group, isobutyl group, tert-butyl group and the like, and the present invention is not limited only to those exemplified ones. Among the groups of $R^7$, methyl group and ethyl group are preferred, and methyl group is more preferred, from the viewpoint of improvement in hydrophilic property of the aqueous gel substrate and suppression of the adhesion of microphage.

In the hydrophilic monomer represented by the formula (III), $R^8$ is an alkylene group having 1 to 8 carbon atoms. The alkylene group having 1 to 8 carbon atoms includes, for example, methylene group, ethylene group, n-propylene group, isopropylene group, n-butylene group, isobutylene group, tert-butylene group, n-pentene group, cyclopentene group, n-hexene group, isohexene group, cyclohexene group and the like, and the present invention is not limited only to those exemplified ones. Among the groups of $R^8$, an alkylene group having 1 to 6 carbon atoms is preferred, an alkylene group having 1 to 4 carbon atoms is more preferred, methylene group and ethylene group are furthermore preferred, and ethylene group is still more preferred, from the viewpoint of improvement in hydrophilic property of the aqueous gel substrate and suppression of the adhesion of microphage.

In the hydrophilic monomer represented by the formula (III), each of $R^9$ and $R^{10}$ is independently an alkyl group having 1 to 4 carbon atoms. The alkyl group having 1 to 4 carbon atoms includes, for example, methyl group, ethyl group, n-propyl group, isopropyl group, n-butyl group, isobutyl group, tert-butyl group and the like, and the present invention is not limited only to those exemplified ones. Among the groups of $R^9$ and $R^{10}$, methyl group and ethyl group are preferred, and methyl group is more preferred, from the viewpoint of improvement in hydrophilic property of the aqueous gel substrate and suppression of the adhesion of microphage.

In the hydrophilic monomer represented by the formula (III), $R^{11}$ is an alkylene group having 1 to 4 carbon atoms. The alkylene group having 1 to 4 carbon atoms includes, for example, methylene group, ethylene group, n-propylene group, isopropylene group, n-butylene group, isobutylene group, tert-butylene group and the like, and the present invention is not limited only to those exemplified ones. Among the groups of $R^{11}$, methylene group and ethylene group are preferred, and methylene group is more preferred, from the viewpoint of improvement in hydrophilic property of the aqueous gel substrate and suppression of the adhesion of microphage.

In the hydrophilic monomer represented by the formula (III), X is oxygen atom or —NH— group. Among the groups of X, oxygen atom is preferred from the viewpoint of improvement in hydrophilic property of the aqueous gel substrate and suppression of the adhesion of microphage.

The hydrophilic monomer represented by the formula (III) includes, for example, N-acryloyloxyethyl-N,N-dimethylammonium-α-N-methylcarboxybetaine, N-methacryloyloxyethyl-N,N-dimethylammonium-α-N-methylcarboxybetaine, N-acryloyloxyethyl-N,N-diethylammonium-α-N-methylcarboxybetaine, N-methacryloyloxyethyl-N,N-diethylammonium-α-N-methylcarboxybetaine, N-acryloyloxyethyl-N,N-dimethylammonium-β-N-ethylcarboxybetaine, N-methacryloyloxyethyl-N,N-dimethylammonium-β-N-ethylcarboxybetaine, N-acryloyloxyethyl-N,N-diethylammonium-β-N-ethylcarboxybetaine, N-methacryloyloxyethyl-N,N-diethylammonium-β-N-ethylcarboxybetaine and the like, and the present invention is not limited only to those exemplified ones. These hydrophilic monomers can be used alone, respectively, or two or more kinds thereof can be used together. The hydrophilic monomer can be easily prepared by a method as described in, for example, Japanese Unexamined Patent Publication No. HEI 09-95474 A, Japanese Unexamined Patent Publication No. HEI 09-95586, Japanese Unexamined Patent Publication No. HEI 11-222470, and the like.

Among the hydrophilic monomers represented by the formula (III), a hydrophilic monomer in which $R^7$ is methyl group, $R^8$ is ethylene group, each of $R^9$ and $R^{10}$ is methyl group, $R^{11}$ is methylene group, and X is oxygen atom, more specifically, N-methacryloyloxyethyl-N,N-dimethylammonium-α-N-methylcarboxybetaine is preferred from the viewpoint of improvement in hydrophilic property of the aqueous gel substrate and suppression of the adhesion of microphage.

The crosslinkable monomer includes, for example, polyfunctional monomers such as (meth)acrylamide compounds having two or more (meth)acryloyl groups, preferably two (meth)acryloyl groups, such as alkylenebis(meth)acrylamide having an alkylene group of 1 to 4 carbon atoms, such as methylenebisacrylamide and methylenebismethacrylamide; (meth)acrylate compounds having two or more (meth)acryloyl groups, preferably two or three (meth)acryloyl groups, such as ethylene diacrylate, ethylene dimethacrylate, ethylene glycol diacrylate, diethylene glycol diacrylate, ethylene glycol dimethacrylate, diethylene glycol dimethacrylate, triethylene glycol diacrylate, triethylene glycol dimethacrylate, propylene glycol diacrylate, propylene glycol dimethacrylate, 1,4-butanediol diacrylate, 1,4-butanediol dimethacrylate, 1,6-hexanediol diacrylate, 1,6-hexanediol dimethacrylate, 1,9-nonanediol diacrylate, 1,9-nonanediol dimethacrylate, 2-n-butyl-2-ethyl-1,3-propanediol diacrylate, 2-butyl-2-ethyl-1,3-propanediol dimethacrylate, triethylene glycol diacrylate, triethylene glycol dimethacrylate, tripropylene glycol diacrylate, tripropylene glycol dimethacrylate, tetraethylene glycol diacrylate, tetraethylene glycol dimethacrylate, trimethylolpropane triacrylate, trimethylolpropane trimethacrylate, pentaerythritol triacrylate, pentaerythritol trimethacrylate and the like; amine compounds having two or more carbon-carbon double bonds, preferably two or three carbon-carbon double bonds, such as diallylamine and triallylamine; and aromatic compounds having two or more carbon-carbon double bonds, preferably two or three carbon-carbon double bonds, such as divinylbenzene and diallylbenzene; and the present invention is not limited only to those exemplified ones. These crosslinkable monomers can be used alone, respectively, or two or more kinds thereof can be used together.

Among the crosslinkable monomers, a (meth)acrylamide compound having two or more (meth)acryloyl groups, a (meth)acrylate compound having two or more (meth)acryloyl groups, an amine compound having two or more carbon-carbon double bonds, and an aromatic compound having two or more carbon-carbon double bonds are preferred, a (meth)acrylamide compound having two or more (meth)acryloyl groups, a (meth)acrylate compound having two or more (meth)acryloyl groups, and an amine compound having two or more carbon-carbon double bonds are more preferred, a (meth)acrylamide compound having two or more (meth)acryloyl groups and a (meth)acrylate compound having two or more (meth)acryloyl groups are furthermore preferred, a (meth)acrylamide compound having two or more (meth)acryloyl groups is still more preferred, and an alkylenebis(meth)acrylamide having an alkylene group of 1 to 4 carbon atoms is particularly preferred, from the viewpoint of improvement in hydrophilic property of the aqueous gel substrate and effective suppression of the adhesion of microphage. These crosslinkable monomers can be used alone, respectively, or two or more kinds thereof can be used together.

Among the alkylenebis(meth)acrylamides having 1 to 4 carbon atoms, methylenebisacrylamide and methylenebismethacrylamide are preferred from the viewpoint of improvement in hydrophilic property of the aqueous gel substrate and effective suppression of the adhesion of microphage. These alkylenebis(meth)acrylamides can be used alone, respectively, or two or more kinds thereof can be used together.

The amount of the crosslinkable monomer per 100 parts by weight of the hydrophilic monomer is preferably 0.1 to 5 parts by weight and more preferably 0.3 to 3 parts by weight, from the viewpoint of improvement in hydrophilic property of the aqueous gel substrate, effective suppression of the adhesion of microphage, as well as imparting flexibility and feasibility of easy removal of grown cells.

The monomer composition may contain the other monomer within a range which would not hinder an object of the present invention. The other monomers includes, for example, monofunctional monomers such as (meth)acrylic acid alkyl esters having an alkyl group of 1 to 18 carbon atoms, such as methyl acrylate, methyl methacrylate, ethyl acrylate, ethyl methacrylate, n-butyl acrylate, n-butyl methacrylate, isobutyl acrylate, isobutyl methacrylate, tert-butyl acrylate, tert-butyl methacrylate, neopentyl acrylate, neopentyl methacrylate, octyl acrylate, octyl methacrylate, lauryl acrylate, lauryl methacrylate, stearyl acrylate, stearyl methacrylate, cetyl acrylate and cetyl methacrylate; cycloalkyl (meth)acrylates having a cycloalkyl group of 6 to 12 carbon atoms, such as cyclohexyl acrylate and cyclohexyl methacrylate; (meth)acrylic acid aryl esters having an aryl group of 6 to 12 carbon atoms, such as benzyl acrylate and benzyl methacrylate; hydroxyalkyl (meth)acrylates having a hydroxyalkyl group of 2 to 6 carbon atoms, such as hydroxyethyl acrylate, hydroxyethyl methacrylate, hydroxypropyl acrylate, hydroxypropyl methacrylate, hydroxybutyl acrylate and hydroxybutyl methacrylate; alkoxyalkyl (meth)acrylates having an alkoxyalkyl group of 2 to 8 carbon atoms, such as methoxyethyl acrylate, methoxyethyl methacrylate, methoxybutyl acrylate and methoxybutyl methacrylate; alkylcarbitol (meth)acrylates having an alkyl group of 1 to 4 carbon atoms, such as ethylcarbitol acrylate and ethylcarbitol methacrylate; alkyl(meth)acrylamides having an alkyl group of 1 to 12 carbon atoms, such as N-methylacrylamide, N-methylmethacrylamide, N-ethylacrylamide, N-ethylmethacrylamide, N-propylacrylamide, N-propylmethacrylamide, N-isopropylacrylamide, N-isopropylmethacrylamide, N-tert-butylacrylamide, N-tert-butylmethacrylamide, N-octylacrylamide, N-octylmethacrylamide, N,N-dimethylacrylamide, N,N-dimethylmethacrylamide, N,N-diethylacrylamide and N,N-diethylmethacrylamide; alkoxy (meth)acrylamides having an alkoxy group of 1 to 6 carbon atoms, such as N-butoxymethylacrylamide and N-butoxymethylmethacrylamide; (meth)acryloylmorpholines such as acryloylmorpholine and methacryloylmorpholine; diacetone (meth)acrylamides such as diacetoneacrylamide and diacetonemethacrylamide; styrenic monomers such as styrene and methylstyrene; fatty acid alkyl esters having an alkyl group of 1 to 4 carbon atoms other than the (meth)acrylic acid alkyl esters, such as methyl itaconate and ethyl itaconate; fatty acid vinyl esters such as vinyl acetate and vinyl propionate; and nitrogen atom-containing monomers such as N-vinylpyrrolidone and N-vinylcaprolactam. The present invention is not limited only to those exemplified ones. These other monomers can be used alone, respectively, or two or more kinds thereof can be used together.

The atmosphere where the monomer composition is polymerized is not particularly limited. The atmosphere can be the atmospheric are or an inert gas such as nitrogen gas or argon gas.

The polymerization of the monomer composition can be carried out, for example, by a mass polymerization method, a solution polymerization method and the like. When the monomer composition is polymerized by a solution polymerization method, a solvent is used. The solvent includes, for example, water; alcohols such as methyl alcohol, ethyl alcohol, isopropyl alcohol, ethylene glycol and propylene glycol; ketones such as acetone and methyl ethyl ketone; alkyl ethers such as diethyl ether and tetrahydrofuran; aromatic compounds such as benzene, toluene and xylene; hydrocarbon compounds such as n-hexane and cyclohexane; acetic acid esters such as methyl acetate and ethyl acetate, and the present invention is not limited only to those exemplified ones. These solvents can be used alone, respectively, or two or more kinds thereof can be used together. The amount of the solvent cannot be absolutely determined because the amount of the solvent differs depending on the kind of the solvent. It is preferred that the amount of the solvent is usually 300 to 1000 parts by weight or so per 100 parts by weight of the monomer composition.

The polymerization of the monomer composition can be carried out, for example, by a polymerization method such as a radical polymerization method, a living radical polymerization method, an anion polymerization method, a cation polymerization method, an addition polymerization method or a condensation polymerization method.

When the monomer composition is polymerized, a polymerization initiator can be used. The polymerization initiator includes, for example, a thermal polymerization initiator and a photopolymerization initiator.

The thermal polymerization initiator includes, for example, azo-based polymerization initiators such as azoisobutyronitrile, methyl azoisobutyrate and azobisdimethylvalerontrile; and peroxide-based polymerization initiators such as benzoyl peroxide, potassium persulfate and ammonium persulfate, and the present invention is not limited only to those exemplified ones. These polymerization initiators can be used alone, respectively, or two or more kinds thereof can be used together.

When the thermal polymerization initiator is used as a polymerization initiator, it is preferred that the amount of the thermal polymerization initiator is usually 0.01 to 20 parts by weight or so per 100 parts by weight of the monomer composition.

The photopolymerization initiator includes, for example, 2-oxoglutaric acid, 1-hydroxycyclohexyl phenyl ketone, 2-hydroxy-2-methyl-1-phenylpropan-1-one, 2-methyl[4-(methylthio)phenyl]-2-morpholinopropan-1-one, 2,2-dimethoxy-1,2-diphenylethan-1-one, benzophenone, 1-[4-(2-hydroxyethoxy)phenyl]-2-hydroxy-2-methyl-1-propan-1-one, 2-benzyl-2-dimethylamino-1-(4-morpholinophenyl)butan-1-one, bis(2,6-dimethoxybenzoyl)-2,4,4-trimethylpentylphosphine oxide and the like, and the present invention is not limited only to those exemplified ones. These polymerization initiators can be used alone, respectively, or two or more kinds thereof can be used together.

When the photopolymerization initiator is used as a polymerization initiator, it is preferred that the amount of the photopolymerization initiator is usually 0.01 to 20 parts by weight or so per 100 parts by weight of the monomer composition.

The polymerization temperature of the monomer composition is not particularly limited, and can be usually a temperature of 5 to 80° C. or so. The period of time necessary for the polymerization of the monomer composition cannot be absolutely determined because the period of time for the polymerization differs depending on the polymerization conditions. Therefore, the period of time for the polymerization is arbitrary. The polymerization reaction can be arbitrarily terminated at the time when the amount of the remaining monomer becomes 10% by weight or less. The amount of the remaining monomer can be determined, for example, by adding bromine to the double bond of the monomer, and determining the content of the double bond.

As described above, a crosslinked polymer is obtained by carrying out the polymerization of the monomer composition. Also, as described above, an aqueous gel substrate is obtained by gelling the crosslinked polymer. When the monomer composition is polymerized by a solution polymerization method with water as a solvent, an aqueous gel substrate containing the crosslinked polymer can be directly obtained. Also an aqueous gel substrate can be obtained by adding water to the crosslinked gel to form a gel of the crosslinked polymer. However, it is preferred that an aqueous gal substrate containing the crosslinked polymer is obtained by using water as a solvent, and carrying out the solution polymerization of the monomer composition from the viewpoint of improvement in hydrophilic property of an aqueous gel substrate and effective suppression of the adhesion of microphage.

The water content of the aqueous gel substrate of the present invention obtained in the above is preferably 0.5 to 20% by weight, more preferably 1 to 15% by weight and further preferably 3 to 10% by weight from the viewpoint of improvement in hydrophilic property of the aqueous gel substrate and effective suppression of the adhesion of microphage.

The aqueous gel substrate of the present invention may contain an antibacterial agent, a coloring agent, a perfume and the like in an appropriate amount within a range which would not hider an object of the present invention.

The shape of the aqueous gel substrate of the present invention is arbitrary. When a mold having a predetermined inner surface shape is charged with the above-mentioned monomer composition, and carrying out its polymerization, an aqueous gel substrate having a shape corresponding to the inner surface shape of the molding die can be obtained. Also, when the above-mentioned monomer composition is casted on a substrate, and carrying out its polymerization, a film-like or sheet-like aqueous gel substrate can be obtained. When the aqueous gel substrate of the present invention is used, for example, in uses such as a cell culture sheet, the aqueous gel sheet can be used, for example, as a sheet having a thickness of 5 mm or so.

As described above, the aqueous gel substrate of the present invention is not only excellent in hydrophilic property, but also has a property such that the adhesiveness of macrophages is small. Therefore, the aqueous gel substrate can be suitably used in, for example, a cell culture sheet and the like.

As a process suitable for producing the cell culture sheet of the present invention, there can be cited, for example, a process for producing a sheet-like aqueous gel substrate made of a crosslinked polymer by carrying out the solution polymerization of an aqueous solution of a monomer composition, and the like, and the present invention is not limited only to the process. Concrete examples of the process for producing a sheet-like aqueous gel substrate include a process for carrying out a solution polymerization of an aqueous solution of a monomer composition, which includes charging a vessel with the aqueous solution of a monomer composition so as to have a thickness corresponding to the thickness of a sheet, and carrying out the polymerization of the monomer composition in the vessel; a process for producing a sheet-like cell culture sheet, which includes spreading an aqueous gel substrate obtained by carrying out the solution polymerization of an aqueous solution of a monomer composition so that an obtained aqueous gel substrate has a desired thickness; a process for producing a sheet-like cell culture sheet, which includes slicing an aqueous gel substrate obtained by carrying out the solution polymerization of an aqueous solution of a monomer composition so that an obtained aqueous gel substrate has a desired thickness, and the like. The present invention is not limited only to those methods.

As described above, the cell culture sheet of the present invention is obtained. The size and thickness of the cell culture sheet of the present invention cannot be absolutely determined because the size and thickness differs depending on its use and the like. Therefore, it is preferred that the size and thickness of the cell culture sheet of the present invention are appropriately adjusted in accordance with its use and the like.

A reinforcing material such as a woven fabric, a nonwoven fabric, a resin sheet or a resin film can be provided on the back surface of the cell culture sheet of the present invention as occasion demands. In addition, when a reinforcing material such as a resin sheet or a resin film is provided on the back surface of the cell culture sheet of the present invention, a crosslinked polymer layer made of, for example, a crosslinked polymer having an anionic group, or the like can be formed on the front surface of the reinforcing material from the viewpoint of improvement in affinity between the cell culture sheet and the reinforcing material. The crosslinked polymer having an anionic group can be prepared, for example, by carrying out the polymerization of a monomer component such as acrylamidomethylpropanesulfonic acid or methylenebisacrylamide in a polymerization method such as a solution polymerization method.

The cell culture sheet of the present invention is excellent in not only hydrophilic property but also adhesion resistance to macrophages, and can suppress differentiation at the time of culturing of ES cells and dedifferentiation. Accordingly, the cell culture sheet can be preferably used as, for example, a cell culture sheet for suppressing adhesion of macrophage.

EXAMPLES

Next, the present invention will be more specifically described below based on working examples, but the present invention is not limited only to those examples.

Example 1

A cubic cuvette having 10 cm each side, made of a transparent resin film having a thickness of 5 mm was prepared.

Next, 14.1 g of acrylamidomethylpropanesulfonic acid (AMPS), 0.6 g of methylenebisacrylamide (MBAA) and 0.01 g of 2-oxoglutaric acid as a photopolymerization initiator were dissolved in 100 g of distilled water, to give a solution A.

On the other hand, 18.6 g of N-methacryloyloxyethyl-N, N-dimethylammonium-$\alpha$-N-methylcarboxybetaine (CDME), 1.4 g of acrylamide, 0.0014 g of methylenebisacrylamide (MBAA) and 0.001 g of 2-oxoglutaric acid were dissolved in 100 g of distilled water, to give a solution B.

Next, the cuvette was charged with the solution A, and irradiated with an ultraviolet ray at an illuminance of 4 mW/cm$^2$ for an irradiation period of time of 6 hours in an integrated light amount of 86.4 J/cm² from its side with an ultraviolet irradiating machine [Manufactured by UVP, LLC under the model number of 95-0042-12]. Thereafter, the cuvette was charged with the solution B, and the resulting solution was stirred so as to be uniform. The solution was then irradiated again with an ultraviolet ray at an illuminance of 4 mW/cm² for an irradiation period of time of 6 hours in an integrated light amount of 86.4 J/cm² from its side with the ultraviolet irradiating machine, to give a gel.

The gel obtained in the above was taken out from the cuvette, and was cut with a cutter knife so as to have a length of 9 cm and a width of 5 mm, to give a sample 1.

Example 2

A sample 2 was obtained in the same manner as in Example 1 except that the amount of N-methacryloyloxyethyl-N, N-dimethylammonium-α-N-methylcarboxybetaine (CDME) was changed to 37.2 g, and that the amount of methylenebisacrylamide (MBAA) was changed to 0.0042 g in Example 1.

Example 3

A sample 3 was obtained in the same manner as in Example 1 except that the amount of N-methacryloyloxyethyl-N, N-dimethylammonium-α-N-methylcarboxybetaine (CDME) was changed to 55.8 g, and that the amount of methylenebisacrylamide (MBAA) was changed to 0.0042 g in Example 1.

Comparative Example 1

A cubic cuvette having 10 cm each side, made of a transparent resin film having a thickness of 5 mm was prepared.

Next, 14.1 g of acrylamidomethylpropanesulfonic acid (AMPS), 0.6 g of methylenebisacrylamide (MBAA) and 0.01 g of 2-oxoglutaric acid were dissolved in 100 g of distilled water to give a solution A.

On the other hand, 1.4 g of acrylamide, 0.0007 g of methylenebisacrylamide (MBAA) and 0.001 g of 2-oxoglutaric acid were dissolved in 100 g of distilled water to give a solution B.

Next, the cuvette was charged with the solution A, and irradiated with an ultraviolet ray at an illuminance of 4 mW/cm² for an irradiation period of time of 6 hours in an integrated light amount of 86.4 J/cm² from its side with an ultraviolet irradiating machine [manufactured by UVP, LLC under the model number of 95-0042-12]. Thereafter, the cuvette was charged with the solution B, and the resulting solution was stirred so as to be uniform. Next, the solution was irradiated again with an ultraviolet ray at an illuminance of 4 mW/cm² for an irradiation period of time of 6 hours in an integrated light amount of 86.4 J/cm² from its side with the ultraviolet irradiating machine to give a gel.

Next, the gel obtained in the above was taken out from the cuvette, and was cut with a cutter knife so as to have a length of 9 cm and a width of 5 mm, to give a comparative sample 1.

As the physical properties of the samples 1 to 3 obtained in Examples 1 to 3 and the comparative sample 1 obtained in Comparative Example 1, tensile strength and Young's modulus were determined by using a tensile testing machine [manufactured by Orientec Co., Ltd. under the model number of Tensilon RTC-1310A]. The results of the determined tensile strength are shown in FIG. 1, and the results of the determined Young's modulus are shown in FIG. 2. In FIG. 1, symbols A to D show the test results of the samples 1 to 3 obtained in Examples 1 to 3 and the comparative sample 1 obtained in Comparative Example 1 in this order, respectively.

From the results shown in FIG. 1, it can be seen that all of the samples 1 to 3 obtained in Examples 1 to 3 are excellent in tensile stress (stress) even in a region where a strain is about 4.5 mm or more, as compared with the comparative sample 1 obtained in Comparative Example 1. From the results shown in FIG. 2, it can be also seen that the samples 1 to 3 obtained in Examples 1 to 3 exhibit equal to or superior modulus (Young's modulus), as compared with the modulus of the comparative sample 1 obtained in Comparative Example 1. Therefore, it can be seen that all of the samples 1 to 3 obtained in Examples 1 to 3 exhibit excellent effects such that the gel strength is hardly lowered, and that flexibility and mechanical strength are simultaneously satisfied, as compared with the comparative sample 1 obtained in Comparative Example 1.

Example 4

A cubic cuvette having 10 cm each side, made of a transparent resin film having a thickness of 5 mm was prepared.

Next, 14.1 g of acrylamidomethylpropanesulfonic acid (AMPS), 0.6 g of methylenebisacrylamide (MBAA) and 0.01 g of 2-oxoglutaric acid as a photopolymerization initiator were dissolved in 100 g distilled water to give a solution A.

On the other hand, 18.6 g of N-methacryloyloxyethyl-N, N-dimethylammonium-α-N-methylcarboxybetaine, 0.15 g of methylenebisacrylamide and 0.015 g of 2-oxoglutaric acid were dissolved in 100 g of distilled water to give an aqueous solution of a monomer composition (solution B).

Next, the cuvette was charged with the solution A, and irradiated with an ultraviolet ray at an illuminance of 4 mW/cm² for an irradiation period of time of 6 hours in an integrated light amount of 86.4 J/cm² from its side with an ultraviolet irradiating machine [manufactured by UVP, LLC under the model number of 95-0042-12], to form a crosslinked polymer layer made of an acrylamidomethylpropanesulfonic acid-methylenebisacrylamide copolymer on a resin film. Thereafter, the cuvette was charged with the solution B, and stirred so as to be uniform. Next, the solution was irradiated again with an ultraviolet ray at an illuminance of 4 mW/cm² for an irradiation period of time of 6 hours in an integrated light amount of 86.4 J/cm² from its side, to prepare an aqueous gel substrate having a thickness of about 1 mm. When the contact angle of water to this aqueous gel substrate was measured with a dynamic wettability tester (manufactured by RHESCA Corporation under the model number of WET-6000), the contact angle was 0 degree. From this fact, it was confirmed that the aqueous gel sheet was excellent in hydrophilic property. This aqueous gel substrate was used as a cell culture sheet.

Example 5

An aqueous gel substrate was prepared in the same manner as in Example 4 except that the amount of methylenebisacrylamide was changed to 0.10 g in Example 4. When the contact angle of water to this aqueous gel substrate was measured in the same manner as in Example 4, the contact angle was 0 degree. From this fact, it was confirmed that the aqueous gel substrate was excellent in hydrophilic property. This aqueous gel substrate was used as a cell culture sheet.

Example 6

An aqueous gel substrate was prepared in the same manner as in Example 4 except that the amount of methylenebisacrylamide was changed to 0.30 g in Example 4. When the contact angle of water to this aqueous gel substrate was measured in the same manner as in Example 4, the contact angle was 0 degree. From this fact, it was confirmed that the aqueous gel substrate was excellent in hydrophilic property. This aqueous gel substrate was used as a cell culture sheet.

Example 7

An aqueous gel substrate was prepared in the same manner as in Example 4 except that 0.15 g of ethylene glycol diacrylate was used in place of methylenebisacrylamide in Example 4. When the contact angle of water to this aqueous gel substrate was measured in the same manner as in Example 4, the contact angle was 0 degree. From this fact, it was confirmed that the aqueous gel substrate was excellent in hydrophilic property. This aqueous gel substrate was used as a cell culture sheet.

Example 8

An aqueous gel substrate was prepared in the same manner as in Example 4 except that 0.20 g of triallylamine was used in place of methylenebisacrylamide in Example 4. When the contact angle of water to this aqueous gel substrate was measured in the same manner as in Example 4, the contact angle was 0 degree. From this fact, it was confirmed that the aqueous gel substrate was excellent in hydrophilic property. This aqueous gel substrate was used as a cell culture sheet.

Comparative Example 2

A cubic cuvette having 10 cm each side, made of a transparent resin film having a thickness of 5 mm was prepared.

Next, 14.1 g of acrylamidomethylpropanesulfonic acid (AMPS), 0.6 g of methylenebisacrylamide (MBAA) and 0.01 g of 2-oxoglutaric acid as a photopolymerization initiator were dissolved in 100 g of distilled water to give a solution A.

On the other hand, 7.0 g of acrylamide, 0.6 g of methylenebisacrylamide and 0.01 g of 2-oxoglutaric acid were dissolved in 100 g of distilled water to give an aqueous solution of a monomer composition (solution B).

Next, the cuvette was charged with the solution A, and irradiated with an ultraviolet ray at an illuminance of 4 mW/cm$^2$ for an irradiation period of time of 6 hours in an integrated light amount of 86.4 J/cm$^2$ from its side with an ultraviolet irradiating machine [manufactured by UVP, LLC under the model number of 95-0042-12], to form a crosslinked polymer layer made of an acrylamidoethylpropanesulfonic acid-methylenebisacrylamide copolymer on a resin film. Thereafter, the cuvette was charged with the solution B, and stirred so as to be uniform. Next, the solution was irradiated again with an ultraviolet ray at an illuminance of 4 mW/cm$^2$ for an irradiation period of time of 6 hours in an integrated light amount of 86.4 J/cm$^2$ from its side with the ultraviolet irradiating machine, to give an aqueous gel substrate. The resulting aqueous gel substrate was used as a cell culture sheet.

Comparative Example 3

A cubic cuvette having 10 cm each side, made of a transparent resin film having a thickness of 5 mm was prepared.

Next, 14.1 g of acrylamidonemethylpropanesulfonic acid (AMPS), 0.6 g of methylenebisacrylamide (MBAA) and 0.01 g of 2-oxoglutaric acid as a photopolymerization initiator were dissolved in 100 g of distilled water to give a solution A.

On the other hand, 9.9 g of dimethylacrylamide, 0.45 g of methylenebisacrylamide (MBAA) and 0.015 g of 2-oxoglutaric acid were dissolved in 100 g of distilled water to give an aqueous solution of a monomer composition (solution B).

Next, the cuvette was charged with the solution A, and irradiated with an ultraviolet ray at an illuminance of 4 mW/cm$^2$ for an irradiation period of time of 6 hours in an integrated light amount of 86.4 J/cm$^2$ from its side with an ultraviolet irradiating machine [manufactured by UVP, LLC under the model number of 95-0042-12], to form a crosslinked polymer layer made of an acrylamidomethylpropanesulfonic acid-methylenebisacrylamide copolymer on a resin film. Thereafter, the cuvette was charged with the solution B, and stirred so as to be uniform. Next, the solution was irradiated again with an ultraviolet ray at an illuminance of 4 mW/cm$^2$ for an irradiation period of time of 6 hours in an integrated light amount of 86.4 J/cm$^2$ from its side with the ultraviolet irradiating machine, to give an aqueous gel substrate. The resulting aqueous gel substrate was used as a cell culture sheet.

Comparative Example 4

In accordance with "Example 1" described in Japanese Unexamined Patent Publication No. 2010-57745, a glass plate having a polymer brush was produced, and the resulting glass plate having a polymer brush was used as a cell culture sheet.

Comparative Example 5

As a cell culture sheet, a cell culture sheet made of polystyrene was used.

Comparative Example 6

As a cell culture sheet, a cell culture sheet made of polystyrene, the surface of which was treated by irradiating with discharge plasma, was used.

Next, each of cell culture sheets obtained in Examples 4 to 8 and Comparative Examples 2 to 6 was placed on the bottom of a petri dish, and the adhesiveness of macrophages was evaluated in accordance with the following method for evaluating adhesiveness of macrophages.

[Method for Evaluating Adhesiveness of Macrophages]

Macrophages were placed on each of the cell culture sheets obtained in Examples 4 to 8 and Comparative Examples 2 to 6 at a concentration of $5.0 \times 10^4$ cells/mL, and the macrophages were cultured in an atmosphere of 37° C. for 24 hours. Thereafter, the cell culture sheets were washed with pure water. The adhesiveness was evaluated by counting the number of cells remaining on the cell culture sheet after washing with water.

As a result, according to the cell culture sheets obtained in Examples 4 to 8, the remaining number of macrophages was 0 cells/mL, and adhesion of microphages was not found at all. In contrast, according to the cell culture sheet obtained in Comparative Example 2, the number of macrophages adhered was 10 cells/mL. According to the cell culture sheet obtained in Comparative Example 3, the number of macrophages adhered was 4 cells/mL. According to the cell culture sheet obtained in Comparative Example 4, the number of macrophages adhered was 0 cells/mL. According to the commercially available cell culture sheet used in Comparative Example 5, the number of macrophages adhered was 38 cells/mL. According to the commercially available cell culture sheet used in Comparative Example 6, the number of macrophages adhered was 143 cells/mL.

From the above results, it can be seen that since all of the cell culture sheets obtained in Examples 4 to 8 are excellent in hydrophilic property, small in adhesiveness to macrophages, and hardly adhere to macrophages, the cell culture sheets can suppress the degeneration of macrophages due to the adhesion of the macrophages to a cell culture sheet, and secretion of an inflammatory protein.

Next, as to the cell culture sheets obtained in Examples 4 to 8 and the cell culture sheet obtained in Comparative Example 4, pencil hardness of each surface of the culture sheets was examined. As a result, the pencil hardness of each surface of the culture sheets obtained in Examples 4 to 8 was 4B, whereas the pencil hardness of the surface of the cell culture sheet obtained in Comparative Example 4 was 9H. From this fact, it was confirmed that all of the cell culture sheets obtained in Examples 4 to 8 were excellent in flexibility.

The easiness of removing grown cells from the cell culture sheet was examined by using tweezers. As a result, the grown cells could be easily removed from the cell culture sheets obtained in Examples 4 to 8 with tweezers. In contrast, since the surface of the cell culture sheet obtained in Comparative Example 4 was hard, it was difficult to remove the grown cells from the sheet with tweezers, and when the grown cells were forcibly removed, cells were liable to be damaged.

Next, the cell culture sheets obtained in Examples 4 to 8 were used, and macrophages were collected from the washing water which was generated when the cell culture sheets were washed with water in the process for evaluating the adhesiveness of macrophages. The collected macrophages were placed on each of the cell culture sheets obtained in Examples 4 to 8, and cultured in an atmosphere of 37° C. for 24 hours. As a result, it was confirmed that macrophages increased. From this fact, it can be seen that macrophages can be increased by using the cell culture sheets obtained in Examples 4 to 8 even when the macrophages are seeded again.

Thereafter, the macrophages obtained in the above were again seeded on the cell culture sheets obtained in Examples 4 to 8, and increased. Thereafter, the adhesiveness of macrophages was evaluated in the same manner as described above. As a result, the remaining number of the macrophages was 0 cell/mL, and adhesion of macrophages was not observed. From this fact, it can be seen that all of the cell culture sheets obtained in Examples 4 to 8 can be repeatedly used.

INDUSTRIAL APPLICABILITY

The aqueous gel of present invention is expected to be used in medicines such as a poultice, an adhesive plaster, a bedsore preventing material, and a would covering material; quasi drugs; and medical materials such as a drug delivery system material, a pH adjusting agent, a molding assistant, a wrapping material, an artificial blood vessel, a blood dialysis membrane, a catheter, a contact lens, an artificial crystalline lens, a blood filter, a blood preserving pack, an artificial organ, a biochip, a cell culture sheet, a sugar chain synthesizer and a molecular shaperon material. In addition, the aqueous gel of the present invention is expected to be applied to the wide range of fields such as cosmetics such as a hair cosmetic, a hair dye, a moisturizing cream, a cleansing cream, a shampoo, a rinse and a lipstick; toiletry products such as an aromatic, a deodorant and a liquid detergent; coating materials for the adhesive surface of a protective film, a self-repairing film and the like, a ship bottom paint, a highly elastic paint for an automobile, a self-repairing paint, an anti-fog paint and an antifouling paint; printing materials such as a screen printing ink and an offset ink; electric or electronic materials such as battery materials such as an electrolyte for flexible battery; actuator materials such as artificial muscle and a piezoelectric element.

In addition, the cell culture sheet of the present invention is not only excellent in hydrophilic property, but also small in adhesiveness to macrophages. The cell culture sheet is furthermore excellent in flexibility, and grown cell can be easily removed from the cell culture sheet. Therefore, it is expected that the cell culture sheet is used, for example, as a cell culture sheet which suppresses differentiation at the time of culturing of ES cells and dedifferentiation.

The invention claimed is:
1. An aqueous gel prepared by gelling a polymer composition comprising a polymer A prepared by carrying out the polymerization of a monomer composition comprising a betaine monomer represented by the formula (I):

[Chemical formula 1]

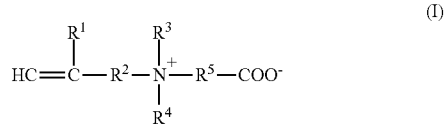

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition comprising an acidic monomer represented by the formula (II):

[Chemical formula 2]

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

2. The aqueous gel according to claim 1, wherein in the betaine monomer represented by the formula (I), $R^1$ is hydrogen atom or an alkyl group having 1 to 6 carbon atoms which may have hydroxyl group or a halogen atom; $R^2$ is —COO— group or —CONH— group; each of $R^3$ and $R^4$ is methyl group, respectively; and $R^5$ is methylene group.

3. The aqueous gel according to claim 1, wherein the molar ratio of the functional group of the polymer A to the functional group of the polymer B is 0.5/1 to 1.5/1.

4. A process for producing an aqueous gel according to claim 1, which comprises carrying out a solution polymerization of an aqueous solution of a monomer composition comprising an acidic monomer to give polymer B, mixing the resulting polymer B with an aqueous solution of a monomer composition comprising a betaine monomer to form a homogeneous mixture, and carrying out a solution polymerization of the resulting mixture to prepare a polymer A; or carrying out a solution-polymerization of an aqueous solution of a monomer composition comprising a betaine monomer to give a polymer A, mixing the resulting polymer A with a monomer composition comprising an acidic monomer to form a homogeneous mixture, and carrying out the solution-polymerization of the resulting mixture to prepare a polymer B.

5. A medical device comprising aqueous gel prepared by gelling a polymer composition comprising a polymer A prepared by carrying out the polymerization of a monomer composition comprising a betaine monomer represented by the formula (I):

[Chemical formula 1]

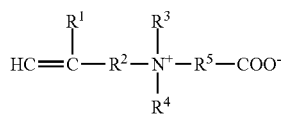

(I)

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition comprising an acidic monomer represented by the formula (II):

[Chemical formula 2]

(II)

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

6. A cosmetic composition comprising aqueous gel prepared by gelling a polymer composition comprising a polymer A prepared by carrying out the polymerization of a monomer composition comprising a betaine monomer represented by the formula (I):

[Chemical formula 1]

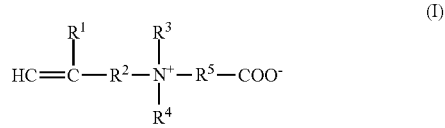

(I)

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition comprising an acidic monomer represented by the formula (II):

[Chemical formula 2]

(II)

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

7. A toiletry article comprising aqueous gel prepared by gelling a polymer composition comprising a polymer A prepared by carrying out the polymerization of a monomer composition comprising a betaine monomer represented by the formula (I):

[Chemical formula 1]

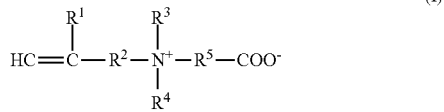

(I)

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition comprising an acidic monomer represented by the formula (II):

[Chemical formula 2]

(II)

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

8. A coating material comprising aqueous gel prepared by gelling a polymer composition comprising a polymer A prepared by carrying out the polymerization of a monomer composition comprising a betaine monomer represented by the formula (I):

[Chemical formula 1]

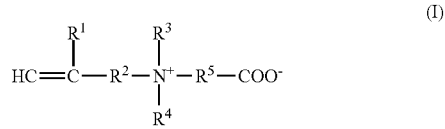

(I)

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition comprising an acidic monomer represented by the formula (II):

[Chemical formula 2]

(II)

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

9. An electric or electronic material comprising aqueous gel prepared by gelling a polymer composition comprising a polymer A prepared by carrying out the polymerization of a monomer composition comprising a betaine monomer represented by the formula (I):

[Chemical formula 1]

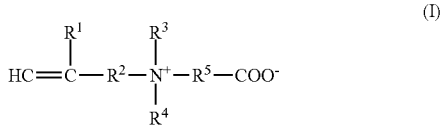

(I)

wherein $R^1$ is hydrogen atom or an alkyl group having 1 to 6 carbon atoms which may have hydroxyl group or a halogen atom; $R^2$ is an alkylene group having 1 to 6 carbon atoms which may have hydroxyl group, an arylene group having 6 to 12 carbon atoms, an aralkylene group having 7 to 12 carbon atoms, —COOH— group or —CONH— group; each of $R^3$ and $R^4$ is independently an alkyl group having 1 to 18 carbon atoms; and $R^5$ is an alkylene group having 1 to 8 carbon atoms, and a polymer B prepared by carrying out the polymerization of a monomer composition comprising an acidic monomer represented by the formula (II):

[Chemical formula 2]

(II)

wherein $R^1$ is hydrogen atom or an alkyl group having 1 to 6 carbon atoms which may have hydroxyl group or a halogen atom; $R^6$ is sulfonic acid group or a neutralized group thereof; phosphoric acid group or a neutralized group thereof; an alkyl group having 1 to 6 carbon atoms having sulfonic acid group or a neutralized group thereof, or phosphoric acid group or a neutralized group thereof, which may have a halogen atom; an aryl group having 6 to 12 carbon atoms having sulfonic acid group or a neutralized group thereof, or phosphoric acid group or a neutralized group thereof; an aralkyl group having 7 to 12 carbon atoms having sulfonic acid group or a neutralized group thereof, or phosphoric acid group or a neutralized group thereof; carboxyl group having sulfonic acid group or a neutralized group thereof, or phosphoric acid group or a neutralized group thereof; or an amino group having sulfonic acid group or a neutralized group thereof, or phosphoric acid group or a neutralized group thereof.

10. The aqueous gel according to claim 1, wherein the betain monomer is at least one betain monomer selected from the group consisting of N-acryloyloxyethyl-N,N-dimethylammonium-α-N-methylcarboxybetaine, N-methacryloyloxyethyl-N,N-dimethylammonium-α-N-methylcarboxybetaine, N-acryloyloxyethyl-N,N-diethylammonium-α-N-methylcarboxybetaine, N-methacryloyloxyethyl-N,N-diethylammonium-α-N-methylcarboxybetaine, N-acryloyloxyethyl-N,N-dimethylammonium-β-N-ethylcarboxybetaine, N-methacryloyloxyethyl-N,N-dimethylammonium-β-N-ethylcarboxybetaine, N-acryloyloxyethyl-N,N-diethylammonium-β-N-ethylcarboxybetaine, N-methacryloyloxyethyl-N,N-diethylammonium-β-N-ethylcarboxybetaine, N-acrylamidopropyl-N,N-dimethylammonium-α-N-methylcarboxybetaine, N-methacrylamidopropyl-N,N-dimethylammonium-α-N-methylcarboxybetaine, N-acrylamidopropyl-N,N-diethylammonium-α-N-methylcarboxybetaine, N-methacrylamidopropyl-N,N-diethylammonium-α-N-methylcarboxybetaine, N-acrylamidopropyl-N,N-dimethylammonium-β-N-ethylcarboxybetaine, N-methacrylamidopropyl-N,N-dimethylammonium-β-N-ethylcarboxybetaine, N-acrylamidopropyl-N,N-diethylammonium-β-N-ethylcarboxybetaine, and N-methacrylamidopropyl-N,N-diethylammonium-β-N-ethylcarboxybetaine.

11. The aqueous gel according to claim 1, wherein the monomer composition containing the betaine monomer further comprises a neutral monomer other than the betaine monomer.

12. The aqueous gel according to claim 11, wherein the neutral monomer is at least one monomer selected from the group consisting of an alkyl (meth)acrylate having an alkyl group of 1 to 18 carbon atoms, a cycloalkyl (meth)acrylates having a cycloalkyl group of 6 to 12 carbon atoms, an aryl (meth)acrylate having an aryl group of 6 to 12 carbon atoms, a hydroxyalkyl (meth)acrylate having a hydroxyalkyl group of 2 to 6 carbon atoms, an alkoxyalkyl (meth)acrylate having an alkoxyalkyl group of 2 to 8 carbon atoms, an alkylcarbitol (meth)acrylate having an alkyl group of 1 to 4 carbon atoms, an alkyl(meth)acrylamide having an alkyl group of 1 to 12 carbon atoms, an alkoxy(meth)acrylamide having an alkoxy group of 1 to 6 carbon atoms, a (meth)acryloylmorpholine, a diacetone(meth)acrylamide, a styrenic monomer, a fatty acid alkyl ester having an alkyl group of 1 to 4 carbon atoms other than the alkyl (meth)acrylate, a fatty acid vinyl ester, a nitrogen atom-containing monomer, a di- or tri(meth)acrylate, a (meth)acrylamide having two or more carbon-carbon double bonds, an aromatic compound having two or more carbon-carbon double bonds, an amine compound having two or more allyl groups, and a (meth)acrylamide compound having two or more carbon-carbon double bonds.

13. The aqueous gel according to claim 11, wherein the content of the neutral monomer in the monomer composition containing the betaine monomer is 20 to 90% by weight.

14. The aqueous gel according to claim 11, wherein the content of the betaine monomer in the monomer composition containing the betaine monomer is 10 to 80% by weight.

15. The aqueous gel according to claim 1, wherein the acidic monomer represented by the formula (II) is at least one monomer selected from the group consisting of vinylsulfonic acid, styrene parasulfonic acid, allylsulfonic acid, acrylamidomethylpropanesulfonic acid, methacrylamidomethylpropanesulfonic acid, ethylene oxide-modified phosphoric acid acrylate and ethylene oxide-modified phosphoric acid acrylate.

16. The aqueous gel according to claim 1, wherein the monomer composition containing the acidic monomer further comprises a neutral monomer.

17. The aqueous gel according to claim 16, wherein the neutral monomer is at least one monomer selected from the group consisting of an alkyl (meth)acrylate having an alkyl group of 1 to 18 carbon atoms, a cycloalkyl (meth)acrylate having a cycloalkyl group of 6 to 12 carbon atoms, an aryl (meth)acrylate having an aryl group of 6 to 12 carbon atoms, a hydroxyalkyl (meth)acrylate having a hydroxyalkyl group of 2 to 6 carbon atoms, an alkoxyalkyl (meth)acrylate having an alkoxyalkyl group of 2 to 8 carbon atoms, an alkylcarbitol (meth)acrylate having an alkyl group of 1 to 4 carbon atoms, an alkyl(meth)acrylamide having an alkyl group of 1 to 12 carbon atoms, an alkoxy(meth)acrylamide having an alkoxy group of 1 to 6 carbon atoms, a (meth)acryloylmorpholine, a diacetone(meth)acrylamide, a styrenic monomer, a fatty acid alkyl ester having an alkyl group of 1 to 4 carbon atoms other than the alkyl (meth)acrylate, a fatty acid vinyl ester, a nitrogen atom-containing monomer, a di- or tri(meth)acrylate, a (meth)acrylamide having two or more carbon-carbon double bonds, an aromatic compound having two or more carbon-carbon double bonds, an amine compound having two or more allyl groups, and a (meth)acrylamide compound having two or more carbon-carbon double bonds.

18. The aqueous gel according to claim 16, wherein the content of the neutral monomer in the monomer composition containing the acidic monomer is 20 to 95% by weight.

19. The aqueous gel according to claim 16, wherein the content of the acidic monomer in the monomer composition containing the acidic monomer is 5 to 80% by weight.

* * * * *